United States Patent
Yoshida et al.

(10) Patent No.: US 10,188,352 B2
(45) Date of Patent: Jan. 29, 2019

(54) ACNE-AFFECTED SKIN DETERMINATION METHOD AND ACNE-AFFECTED SKIN DETERMINATION DEVICE

(71) Applicant: FUJIFILM Corporation, Tokyo (JP)

(72) Inventors: Naoko Yoshida, Kanagawa (JP); Noriko Ohira, Kanagawa (JP)

(73) Assignee: FUJIFILM Corporation, Minato-Ku, Tokyo (JP)

( * ) Notice: Subject to any disclaimer, the term of this patent is extended or adjusted under 35 U.S.C. 154(b) by 377 days.

(21) Appl. No.: 14/976,889

(22) Filed: Dec. 21, 2015

(65) Prior Publication Data

US 2016/0143595 A1     May 26, 2016

Related U.S. Application Data

(63) Continuation of application No. PCT/JP2014/061288, filed on Apr. 22, 2014.

(30) Foreign Application Priority Data

Jun. 28, 2013  (JP) .................................. 2013-137266

(51) Int. Cl.
    *A61B 5/053*    (2006.01)
    *A61B 5/00*     (2006.01)
    *G06F 19/00*    (2018.01)

(52) U.S. Cl.
    CPC .......... *A61B 5/7275* (2013.01); *A61B 5/0537* (2013.01); *A61B 5/443* (2013.01); *G06F 19/00* (2013.01)

(58) Field of Classification Search
    USPC .................................................. 600/306, 600
    See application file for complete search history.

(56) References Cited

FOREIGN PATENT DOCUMENTS

JP     2007-199053 A     8/2007

OTHER PUBLICATIONS

International Preliminary Report on Patentability issued from the International Bureau in counterpart International Application No. PCT/JP2014/061288, dated Jan. 7, 2016.

*Primary Examiner* — Christian Jang
*Assistant Examiner* — Mitchell E Alter
(74) *Attorney, Agent, or Firm* — Sughrue Mion, PLLC (57) ABSTRACT

There is provided a acne-affected skin determination method including: setting an upper region and a lower region so as to vertically divide the face of a subject into two regions; acquiring a measurement value of the amount of moisture in the lower region; acquiring a measurement value of the amount of moisture in the upper region; calculating a target moisture value indicating the level of the amounts of moisture distributed in one of the upper region or the lower region and a reference moisture value indicating the level of the amounts of moisture distributed in a reference region including the other of the upper region and the lower region, based on the measurement values of the amounts of moisture in the upper region and the lower region; obtaining the degree of change in moisture of the target moisture value with respect to the reference moisture value; and determining the ease of generation of acne in the face of the subject based on the obtained degree of change in moisture.

9 Claims, 8 Drawing Sheets

ACNE-AFFECTED SKIN DETERMINATION METHOD AND ACNE-AFFECTED SKIN DETERMINATION DEVICE

CROSS-REFERENCE TO RELATED APPLICATIONS

This application is a Continuation of PCT International Application No. PCT/JP2014/061288 filed on Apr. 22, 2014, which claims priority under 35 U.S.C. § 119(a) to Japanese Patent Application No. 2013-137266 filed on Jun. 28, 2013 The above application is hereby expressly incorporated by reference, in its entirety, into the present application.

BACKGROUND OF THE INVENTION

1. Field of the Invention

The present invention relates to an acne-affected skin determination method and an acne-affected skin determination device, and particularly to an acne-affected skin determination method and an acne-affected skin determination device for determining the ease of generation of acne based on the amount of moisture in the skin.

2. Description of the Related Art

In recent years, in a beauty field, various methods for determining the skin on which acne (pimple) is easily generated, which is called the acne-affected skin, are proposed.

For example, JP2007-199053A discloses a skin evaluation method for collecting a horny layer from the skin through tape stripping; detecting horny layer protein involved in adhesion of horny layer cells; and evaluating the skin based on the existence state of horny layer protein in the horny layer. In general, it is considered that acne is generated due to horny layers being multiply layered caused by acceleration of cell adhesion. Therefore, it is possible to determine the acne-affected skin by detecting horny layer protein such as desmoglein involved in the acceleration of cell adhesion.

However, in the skin evaluation method in JP2007-199053A, a large amount of labor is required for detecting horny layer protein and a burden is given to a subject since the skin is collected through tape stripping. Therefore, an acne-affected skin determination method for determining the acne-affected skin, using the amount of moisture in the skin or the amount of oil in the skin, which is obtained through simple measurement, as an index is proposed. For example, determining the acne-affected skin from a large amount of oil on the cheek or the forehead is proposed.

SUMMARY OF THE INVENTION

Figure 12A:
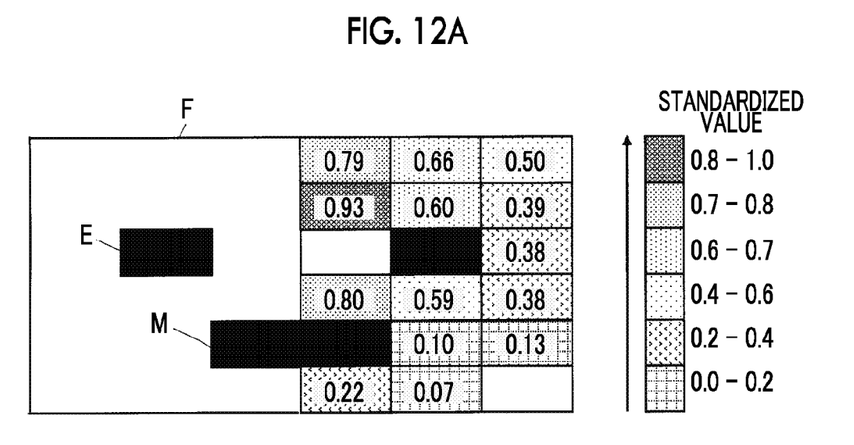
FIG. 12A is a view showing a distribution of the amount of oil on the face of a subject with a large amount of acne and FIG. 12B is a view showing a distribution of the amount of oil on the face of a subject with a small amount of acne.
Figure 12B:
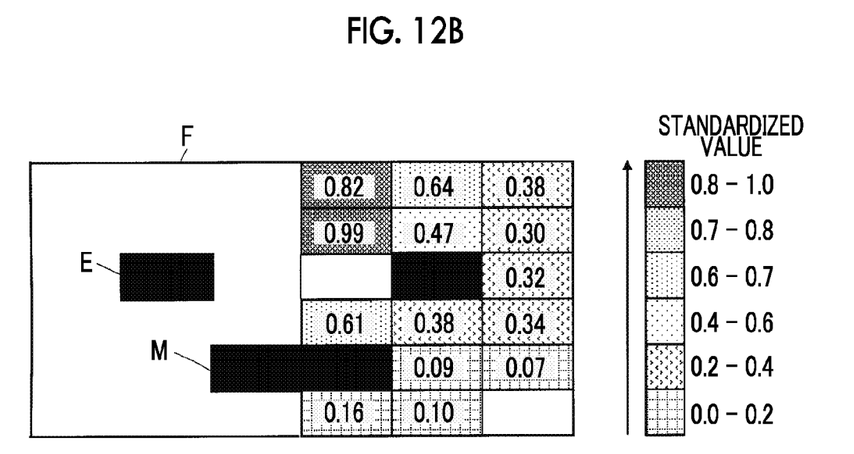

Here, in target subjects of 20 years of age or over, results which are obtained by checking a distribution of oil on the face F of a subject who has a large amount of acne generated in the face F and a subject who has a small amount of acne generated in the face F are shown in FIGS. 12A and 12B. FIGS. 12A and 12B are views in which the amounts of oil in divided regions, in which a left half portion of each face F of the subject with a large amount of acne and the subject with a small amount of acne is divided into sixteen regions, are actually measured, the amounts of obtained oil are standardized within a range of 0.0 to 1.0, and the divided regions are distinguished and are shown in accordance with the standardized values. As shown in FIGS. 12A and 12B, it was found that there is almost no difference in the amounts of oil in the same sites of the faces F of the subject with a large amount of acne and the subject with a small amount of acne, and the distribution of oil on the faces F did not change. Accordingly, it is considered that there is a small influence of the amount of oil on so-called adult acne generated in the subjects of 20 years of age or over. Furthermore, in targeted subjects of 20 years of age or over, the amounts of moisture in the cheek sections of the faces of subjects who had a large amount of acne generated in the face and subjects who had a small amount of acne generated in the face were checked. As a result, there were many subjects who had a number of acne sites even in subjects who had a large amount of moisture in the cheek sections. Therefore, the correlation between the amount of moisture in the cheek section and the amount of acne generated was low. For this reason, it was difficult to accurately determine the acne-affected skin using the amount of moisture and the amount of oil in the skin as indexes.

The present invention has been made to solve such problems in the related art, and an object of the present invention is to provide an acne-affected skin determination method and an acne-affected skin determination device which can accurately determine the acne-affected skin.

A acne-affected skin determination method according to the present invention includes: setting an upper region and a lower region so as to vertically divide the face of a subject into two regions; acquiring a measurement value of the amount of moisture in the lower region; acquiring a measurement value of the amount of moisture in the upper region; calculating a target moisture value indicating the level of the amounts of moisture distributed in one of the upper region or the lower region and a reference moisture value indicating the level of the amounts of moisture distributed in a reference region including the other of the upper region and the lower region, based on the measurement values of the amounts of moisture in the upper region and the lower region; obtaining the degree of change in moisture of the target moisture value with respect to the reference moisture value; and determining the ease of generation of acne in the face of the subject based on the obtained degree of change in moisture.

Here, the target moisture value may indicate the level of the amounts of moisture distributed in the lower region and the reference moisture value may indicate the level of the amounts of moisture distributed in the upper region, and the degree of decrease in moisture of the target moisture value with respect to the reference moisture value may be set to a degree of change in moisture. In addition, the target moisture value may indicate the level of the amounts of moisture distributed in the lower region and the reference moisture value may indicate the level of the amounts of moisture distributed in a region of the entirety of the face, and the degree of decrease in moisture of the target moisture value with respect to the reference moisture value may be set to a degree of change in moisture.

In addition, it is preferable that the upper region and the lower region are regions in which the face of the subject is vertically divided into two sections through a boundary line which is set so as to pass through a space between the height position of the lower end portion of the mouth and the height position of the upper end portion of the eye in the face of the subject.

In addition, with respect to a half section of the face of the subject in which the face is divided by a central line, the half section of the face may be divided horizontally into three regions using a first vertical line which passes through the corner of the mouth from the inner corner of an eye and a second vertical line which passes through the corner of the eye, and the half section of the face may be divided vertically into six regions using a first horizontal line which vertically divides the forehead into two regions, a second horizontal line which passes through a upper end portion of the eye, a third horizontal line which passes through the lower end portion of the eye, a fourth horizontal line which passes through an upper end portion of the mouth, and a fifth horizontal line which passes through the lower end portion of the mouth, so as to divide the half section of the face into sixteen regions except for the eye and the mouth. The regions positioned on an upper side of the third horizontal line may be set to regions A1 to A8, the regions positioned between the third horizontal line and the fourth horizontal line are set to regions A9 to A11 from the central portion to the side portion of the face, and the regions positioned on a lower side of the fourth horizontal line may be set to regions A12 to A16. Therefore, the upper region and the lower region may be set based on the regions A1 to A16.

In addition, the upper region may be formed of the regions A1 to A10 and the lower region may be formed of the regions A11 to A16.

In addition, the upper region may be formed of regions A1 to A9 and the lower region may be formed of regions A10 to A16.

In addition, the upper region may be formed of regions A1 to A11 and the lower region may be formed of regions A12 to A16.

In addition, the degree of change in moisture may be obtained based on the ratio of the target moisture value to the reference moisture value. In addition, the degree of change in moisture may be obtained based on the change of the target moisture value to the reference moisture value.

In addition, it is preferable that the target moisture value is obtained from an average value of amounts of moisture obtained by measuring a plurality of measurement sites within either region of the upper region or the lower region.

In addition, it is preferable that the reference moisture value is obtained from an average value of amounts of moisture obtained by measuring a plurality of measurement sites within the reference region.

In addition, the target moisture value and the reference moisture value may be respectively obtained based on the amounts of moisture in the lower region and the amounts of moisture in the upper region which have been measured within a predetermined period of time immediately before menstruation.

A acne-affected skin determination device according to the present invention includes: a region moisture value calculation unit which sets an upper region and a lower region so as to vertically divide the face of a subject into two regions, acquires a measurement value of the amount of moisture in the lower region, acquires a measurement value of the amount of moisture in the upper region, and calculates a target moisture value indicating the level of the amounts of moisture distributed in one of the upper region and the lower region and a reference moisture value indicating the level of the amounts of moisture distributed in a reference region including the other of the upper region and the lower region, based on the measurement values of the amounts of moisture in the upper region and the lower region; a moisture decrease degree calculation unit which obtains the degree of change in moisture of the target moisture value with respect to the reference moisture value; and an acne-affected skin determination unit which determines the ease of generation of acne in the face of a subject based on the degree of change in moisture which is obtained by the moisture decrease degree calculation unit.

According to the present invention, a target moisture value indicating the level of the amounts of moisture distributed in one of the upper region or the lower region and a reference moisture value indicating the level of the amounts of moisture distributed in a reference region including the other of the upper region and the lower region are calculated; the degree of change in moisture of the target moisture value with respect to the reference moisture value is obtained; and the ease of generation of acne in the face of the subject is determined based on the obtained degree of change in moisture. Therefore, it is possible to accurately determine the acne-affected skin.

DESCRIPTION OF THE PREFERRED EMBODIMENTS

Hereinafter, embodiments of the present invention will be described based on the accompanying drawings.

Embodiment 1

Figure 1:
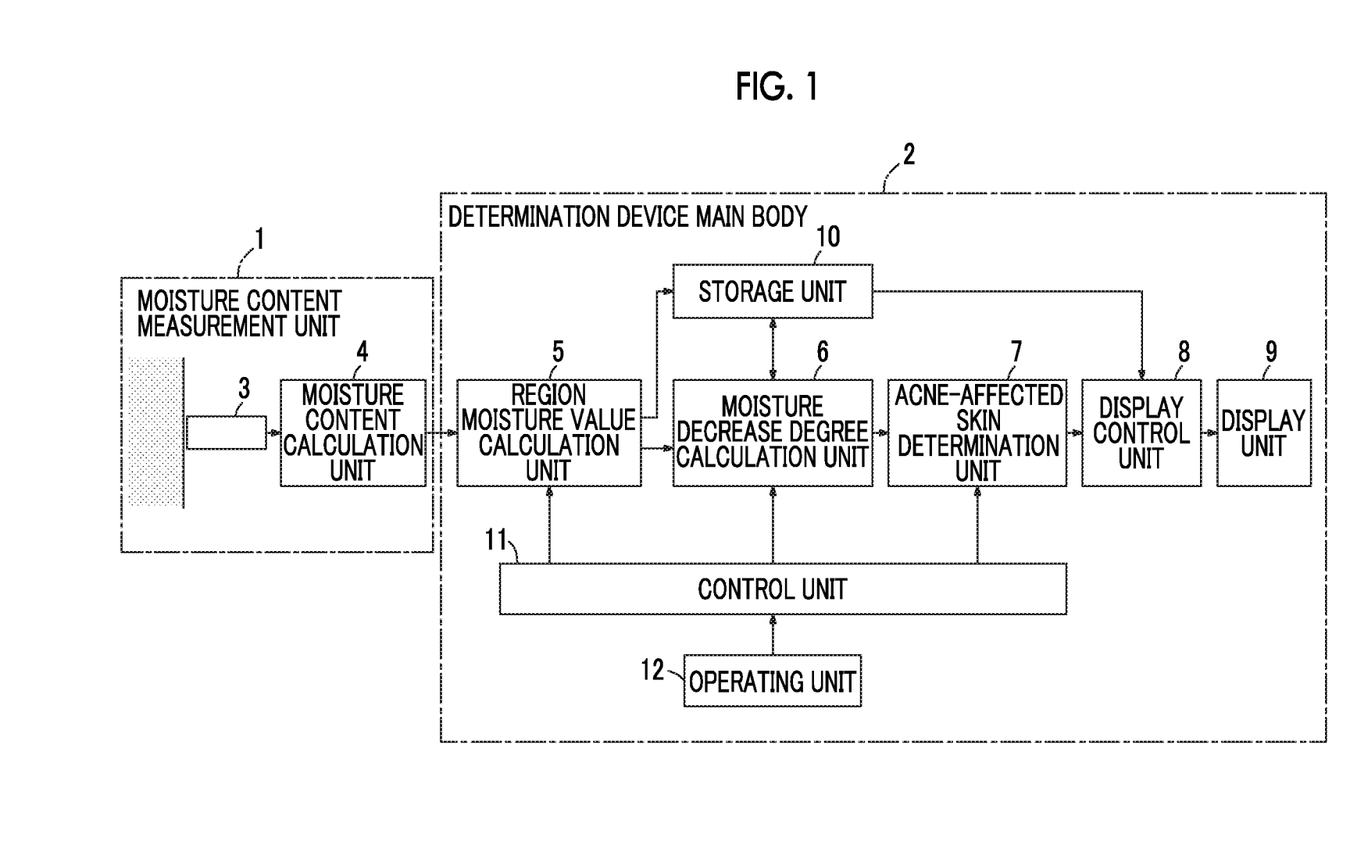
FIG. 1 is a block diagram showing a configuration of an acne-affected skin determination device which performs an acne-affected skin determination method according to Embodiment 1 of the present invention.

FIG. 1 shows a configuration of an acne-affected skin determination device which performs an acne-affected skin determination method according to Embodiment 1 of the present invention. The acne-affected skin determination device determines the acne-affected skin based on the amounts of moisture in an upper region of the face and the amounts of moisture in a lower region of the face when the upper region and the lower region are set so as to vertically divide the face of a subject into two regions. Moreover, the acne-affected skin determination device has a moisture content measurement unit 1 which measures the amounts of moisture in the upper region and the lower region; and a determination device main body 2 which determines the acne-affected skin based on the amounts of moisture which have been measured.

The moisture content measurement unit 1 is constituted of a probe 3 and a moisture content calculation unit 4 by sequentially connecting these to each other.

The probe 3 is used for detecting the amount of moisture in the skin, and a pair of electrodes are disposed at a tip portion of the probe in parallel with an interval kept from each other. A condenser which uses a horny layer (within a range of about 20 μm from the surface of the skin) of the skin as a dielectric is formed by making the tip portion of the probe 3 abut on the skin, and the difference in dielectric constant in accordance with the amount of moisture in the horny layer of the skin is detected as a difference in electrostatic capacity between electrodes. For example, the tip portion of the probe 3 is made to abut on a plurality of measurement sites in the upper region and a plurality of measurement sites in the lower region, and therefore, the electrostatic capacity in accordance with the amount of moisture in the horny layer in each of the measurement sites can be detected.

The moisture content calculation unit 4 calculates the amount of moisture contained in the horny layer of each of the measurement sites based on the electrostatic capacity of the each of the measurement sites which has been detected in the probe 3.

It is possible to use, for example, Corneometer CM820 and Corneometer CM825 (registered trademark) as the moisture content measurement unit 1.

In contrast, the determination device main body 2 includes a region moisture value calculation unit 5 which is connected to the moisture content calculation unit 4 of the moisture content measurement unit 1. A moisture decrease degree calculation unit 6, an acne-affected skin determination unit 7, a display control unit 8, and a display unit 9 are sequentially connected to this region moisture value calculation unit 5. In addition, a storage unit 10 is connected to the region moisture value calculation unit 5, the moisture decrease degree calculation unit 6, and the display control unit 8. Furthermore, a control unit 11 is connected to the region moisture value calculation unit 5, the moisture decrease degree calculation unit 6, the acne-affected skin determination unit 7, and an operating unit 12 is connected to this control unit 11.

The region moisture value calculation unit 5 calculates a reference moisture value indicating the level of the amounts of moisture distributed in an upper region (reference region) and calculates a target moisture value indicating the level of the amounts of moisture distributed in a lower region, based on values which are obtained by measuring the amounts of moisture, which have been input from the moisture content calculation unit 4 of the moisture content measurement unit 1, of a plurality of measurement sites in the upper region of the face of a subject and a value which has been obtained by measuring the amounts of moisture, which have been input from the moisture content calculation unit 4 of the moisture content measurement unit 1, of a plurality of measurement sites in the lower region.

Specifically, the reference moisture value and the target moisture value can be obtained from each moisture content rate in the upper region and the lower region. For example, the reference moisture value can be obtained from an average value of the amounts of moisture which have been obtained by measuring the plurality of measurement sites in the upper region, and the target moisture value can be obtained from an average value of the amounts of moisture which have been obtained by measuring the plurality of measurement sites in the lower region. If the reference moisture value indicates the level of the amounts of moisture distributed in the upper region, the amount of moisture which has been obtained by measuring one measurement site in the upper region may be used. For example, in a case where the amounts of moisture in the plurality of measurement sites in the upper region indicate almost the same values as each other, it is possible to set the amount of moisture in one measurement site to a reference moisture value. Similarly, if the target moisture value indicates the level of the amounts of moisture distributed in the lower region, the amount of moisture which has been obtained by measuring one measurement site in the lower region may be used.

The region moisture value calculation unit 5 outputs the calculated reference moisture value and target moisture value to the moisture decrease degree calculation unit 6 and stores the reference moisture value and target moisture value in the storage unit 10. In addition, the amount of moisture which has been input from the moisture content measurement unit 1 can also be stored in the storage unit 10.

The moisture decrease degree calculation unit 6 obtains the degree of decrease in moisture of the target moisture value with respect to the reference moisture value which has been calculated in the region moisture value calculation unit 5; outputs the obtained degree of decrease in moisture of the target moisture value to the acne-affected skin determination unit 7; and store the degree of decrease in moisture in the storage unit 10.

The acne-affected skin determination unit 7 determines the ease of generation of acne (acne-affected skin) in the face of the subject by evaluating the degree of decrease in moisture which has been input from the moisture decrease degree calculation unit 6 using the information of the degree of decrease in moisture, which has already been obtained by carrying out clinical tests, as an index.

The display control unit 8 displays the determination results of the acne-affected skin, which have been obtained by the acne-affected skin determination unit 7, on the display unit 9. In addition, the display control unit 8 can also display the reference moisture value, the target moisture value, the amounts of moisture in the upper region, the amounts of moisture in the lower region, and the degree of decrease in moisture which have been stored in the storage unit 10 on the display unit 9.

The display unit 9 includes, for example, a display device such as an LCD, and displays the determination results of the acne-affected skin which have been determined by the acne-affected skin determination unit 7 under the control of the display control unit 8.

The storage unit 10 stores the information such as degree of decrease in moisture which has been input from the region moisture value calculation unit 5 and the moisture decrease degree calculation unit 6, and is constituted of, for example, a memory or the like.

The operating unit 12 is a unit through which an operator performs an operation of inputting information, and can be formed of a keyboard, a mouse, a trackball, a touch panel, or the like.

The control unit 11 controls each unit in the acne-affected skin determination device based on various command signals which have been input from the operating unit 12 by an operator.

The region moisture value calculation unit 5, the moisture decrease degree calculation unit 6, the acne-affected skin determination unit 7, the display control unit 8, and the control unit 11 are constituted of a CPU and an operation program for causing the CPU to perform various kinds of processing, but may be constituted of a digital circuit. In addition, it is possible to connect the storage unit 10 to a CPU through a signal line such as a bus. For example, the information such as the degree of decrease in moisture which has been input from the region moisture value calculation unit 5 and the moisture decrease degree calculation unit 6, the determination results of the acne-affected skin obtained in the acne-affected skin determination unit 7 in the past, the information of the degree of decrease in moisture, which has already been obtained by carrying out clinical tests, and the like can be stored in this storage unit 10, and the information stored in the storage unit 10 can be displayed on the display unit 9 under the control of the control unit 11.

Next, the difference between the distributions of the amounts of moisture in the faces of a subject with a large amount of acne and a subject with a small amount of acne will be described.

Figure 2A:
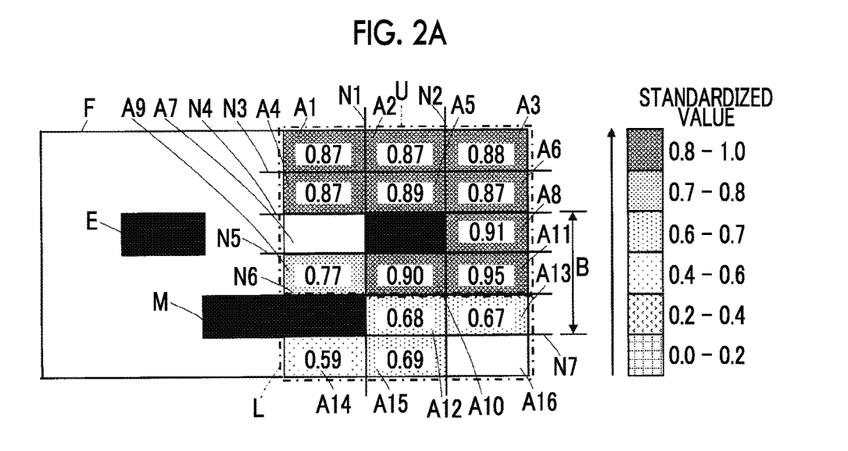
FIG. 2A is a view showing a distribution of the amount of moisture in the face of a subject with a large amount of acne and FIG. 2B is a view showing a distribution of the amount of moisture in the face of a subject with a small amount of acne.
Figure 2B:
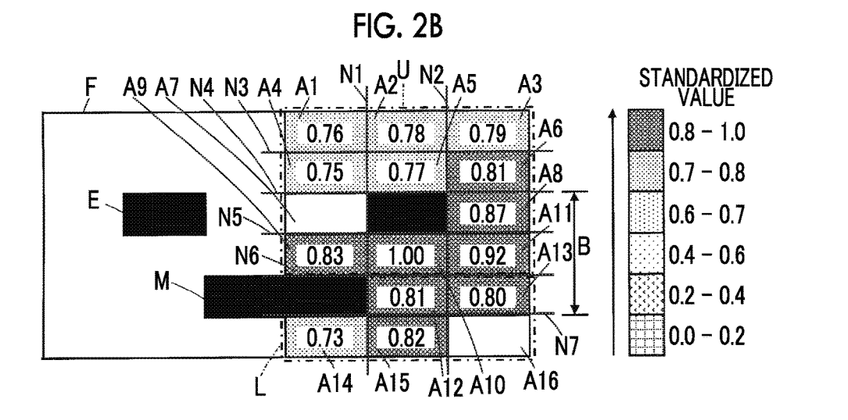

FIGS. 2A and 2B show the distributions of the amounts of moisture in the faces F in a subject with a large amount of acne and subject with a small amount of acne. FIGS. 2A and 2B are views in which the amounts of moisture in divided regions A1 to A16, in which a left half portion of each face F of target subjects of 20 years of age or over is divided into sixteen regions, are actually measured, the obtained amounts of moisture are standardized within a range of 0.0 to 1.0, and the divided regions A1 to A16 are distinguished and shown in accordance with the standardized values.

Here, with respect to the left half section of each face which is divided by a central line passing through the central position of the nose and the mouth M of each face F of a subject, the left half section of the face is divided horizontally into three regions using a first vertical line N1 which passes through the corner of the mouth from the inner corner of an eye and a second vertical line N2 which passes through the corner of the eye, and the left half section of the face F is divided vertically into six regions using a first horizontal line N3 which vertically divides the forehead into two regions, a second horizontal line N4 which passes through a upper end portion of the eye, a third horizontal line N5 which passes through the lower end portion of the eye, a fourth horizontal line N6 which passes through an upper end portion of the mouth, and a fifth horizontal line N7 which passes through the lower end portion of the mouth. Accordingly, the left half section of the face F is divided into 18 divided regions. Among the 18 divided regions which are obtained by dividing the left half section of the face F, 16 divided regions are set to divided regions A1 to A16 except for mouth and eye regions.

Specifically, from the central portion to the side portion of the face, the divided regions positioned on an upper side of the first horizontal line N3 are set to divided regions A1 to A3, the divided regions positioned between the first horizontal line N3 and the second horizontal line N4 are set to divided regions A4 to A6, the divided regions positioned between the second horizontal line N4 and the third horizontal line N5 are set to divided regions A7 and A8, the divided regions positioned between the third horizontal line N5 and the fourth horizontal line N6 are set to divided regions A9 to A11, the divided regions positioned between the fourth horizontal line N6 and the fifth horizontal line N7 are set to divided regions A12 and A13, and the divided regions positioned on a lower side of the fifth horizontal line N7 are set to divided regions A14 to A16.

As shown in FIG. 2A, when the face is divided into two regions of an upper region U and a lower region L at the height position (fourth horizontal line N6) of the upper end portion of the mouth M, the amounts of moisture distributed in the face F of the subject with a large amount of acne indicate high standardized values of greater than or equal to 0.77 in the divided regions A1 to A6 and A8 to A11 included in the upper region U of the face. In contrast, the amounts of moisture thereof indicate low standardized values within a range of 0.59 to 0.69 in the divided regions A12 to A15 included in the lower region L of the face. On the other hand, as shown in FIG. 2B, the amounts of moisture distributed in the face F of the subject with a small amount of acne indicate high standardized values of greater than or equal to 0.73 in all of the divided regions A1 to A6 and A8 to A15, and therefore, no significant change has been found in the upper region U and the lower region L of the face.

Since the divided regions A7 and A16 do not greatly contribute to the determination of the acne-affected skin, the amounts of moisture thereof are not measured. However, the divided regions A7 and A16 are regions having the same amounts of moisture as those of surrounding divided regions and the amounts of moisture thereof are not contrary to the distribution of the above-described amounts of moisture.

Accordingly, it was found that, in the face F of the subject with a large amount of acne, the level value of the amounts of moisture distributed in the lower region L is smaller than that of the amounts of moisture distributed in the upper region U. The amount of moisture of keratin of the skin changes depending on the seasonal difference or the like. However, the tendency of decrease in the amounts of moisture in the lower region L with respect to the upper region U in the face F of the subject with a large amount of acne was observed at all times regardless of season.

Here, in the face F of the subject with a large amount of acne, deterioration in a barrier function occurring in the acne-affected skin is considered as one of the factors for the amounts of moisture in the lower region L decreasing with respect to the upper region U. That is, on the inside of the acne-affected skin, the amount of ceramide in a horny layer is decreased by, for example, increase in an inflammatory factor such as IL-6 and inhibition of gene expression of an enzyme and an enzyme activity which relate to synthesis of a ceramide existing in a horny layer of the skin due to the inflammatory factor. This ceramide takes charge of the barrier function in the horny layer of the skin. The barrier function of the skin also deteriorates if the amount of ceramide in the horny layer decreases, and therefore, the amount of moisture in the horny layer of the skin deteriorates. Accordingly, an abnormality is caused in the turnover (metabolism) due to the skin being dried, thereby resulting in generation of acne. The generation of acne further causes the increase in the inflammatory factor. Therefore, the amount of moisture in the horny layer of the skin is further decreased and acne grows and increases. In this manner, the growth and the increase of acne is caused by the decrease in the amount of moisture in the skin accompanied by the deterioration of the barrier function.

In general, adolescent acne in teens is generated in a so-called T-zone including a nose region and a forehead region of the face. In contrast, acne in subjects of 20 years of age or over is generated in a so-called U-zone including a cheek region and a lower jaw section of the face. For this reason, in the acne-affected skins of subjects of 20 years of age or over, the above-described decrease in the amount of moisture in the U-zone of the face occurs, and it is considered that such a decrease in the amount of moisture in the U-zone which is shown in FIG. 2A causes a decrease in the amounts of moisture distributed in the lower region L of the face.

Accordingly, it can be seen that, in the face F of the subject with a large amount of acne, although a constant amount of moisture is kept in the upper region U, a decrease in the amount of moisture in accordance with the acne-affected skin is caused in the lower region L. For this reason, it is possible to determine the acne-affected skin by obtaining the degree of decrease in moisture of the level value of the amounts of moisture distributed in the lower region L of the face F of the subject with respect to the level value of the amounts of moisture distributed in the upper region U of the face of the subject.

The face F of the subject has been divided into the upper region U and the lower region L having the height position of the mouth M as a boundary, in FIG. 2A. However, the boundary position therebetween significantly changes depending on the subject. Specifically, the boundary position between the upper region U and the lower region L significantly changes within a boundary range B between the height position (fifth horizontal line N7) of the lower end portion of the mouth M and the height position (second horizontal line N4) of the upper end portion of the eye E. For this reason, the position of the boundary line dividing the upper region U and the lower region L is preferably changed within the boundary range B in accordance with the age of the subject or the like.

Next, an operation of Embodiment 1 will be described.

First, in the determination device main body 2 of the acne-affected skin determination device shown in FIG. 1, a boundary line K which vertically divides the face of a subject into two regions of the upper region U and the lower region L is set through an operation of the operating unit 12 performed by an operator.

Figure 3:
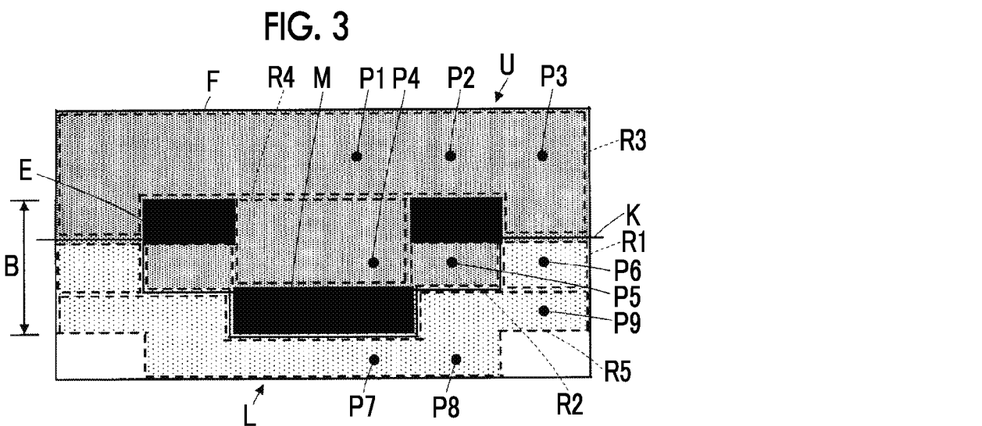
FIG. 3 is a view showing the positions of an upper region and a lower region which are set with respect to the face of a subject.

The boundary line K is set so as to pass through the boundary region B in the face F of the subject. For example, as shown in FIG. 3, the boundary line can be set so as to pass through an upper end portion of the cheek region R1, a lower end portion of an immediately below region R2 of the eye, and a lower end portion of the mouth M. Accordingly, the upper region U is formed of a forehead region R3, a nose region R4, and the immediately below region R2 of the eye, and the lower region L is formed of the cheek region R1 and a jaw skin region R5 which is formed of the skin corresponding to the lower jaw.

Here, the cheek region R1 is formed of the divided region A11, the immediately below region R2 of the eye is formed of the divided region A10, the forehead region R3 is formed of the divided regions A1 to A6 and A8, the nose region R4 is formed of the divided regions A7 and A9, the jaw skin region R5 is formed of the divided regions A12 to 16, the upper region U is formed of divided regions A1 to A10, and the lower region L is formed of divided regions A11 to A16.

Subsequently, an operator sets a measurement site for measuring the amount of moisture within each of the regions of the upper region U and the lower region L. For example, as shown in FIG. 3, it is possible to set 9 measurement sites P1 to P9. Here, the measurement site P1 is positioned slightly next to the center of the forehead region R3, the measurement site P2 is positioned on an upper side in the vicinity of the center of an eyebrow, and the measurement site P3 is positioned on an upper side at the end of the eyebrow, the measurement site P4 is positioned on a side portion of the nose region R4, the measurement site P5 is positioned on a lower side of the corner of the eye, the measurement site P6 is positioned 4 cm or 5 cm inside from an ear in the cheek region R1, the measurement site P7 is positioned slightly next to the center of the jaw skin region R5, the measurement site P8 is positioned on a lower side of the corner of the mouth, and the measurement site P9 is positioned on a side portion of the jaw skin region R5. That is, the measurement sites P1 to P5 are positioned within the upper region U and the measurement sites P6 to P9 are positioned within the lower region L.

The boundary line K and the measurement sites P1 to P9 which are set in the face F of a subject can also be automatically set by the operating unit 12 by keeping the setting conditions or the like in the determination device main body 2 in advance.

Next, the probe 3 of the moisture content measurement unit 1 sequentially abuts on the positions of the measurement sites P1 to P9 of the face F of a subject, and the electrostatic capacity in accordance with the amount of moisture in a horny layer in each of the measurement sites P1 to P9 is detected.

The electrostatic capacity of each of the measurement sites P1 to P9 which has been detected by the probe 3 is output to the moisture content calculation unit 4 which calculates the amount of moisture of each of the measurement sites P1 to P9 based on the electrostatic capacity. The calculated amounts of moisture of the measurement sites P1 to P9 is output to the region moisture value calculation unit 5 of the determination device main body 2 from the moisture content calculation unit 4.

The region moisture value calculation unit 5 classifies the amounts of moisture in the measurement sites P1 to P9 which have been calculated by the moisture content calculation unit 4 into the amounts of moisture in the measurement sites P1 to P5 contained in the upper region U and the amounts of moisture in the measurement sites P6 to P9 contained in the lower region L; the reference moisture value indicating the level of the amounts of moisture distributed in the upper region U is calculated based on the amounts of moisture in the measurement sites P1 to P5; and the target moisture value indicating the level of the amounts of moisture distributed in the lower region L is calculated based on the amounts of moisture in the measurement sites P6 to P9.

Specifically, the reference moisture value can be obtained from an average value of the amounts of moisture in the measurement sites P1 to P5 and the target moisture value can be obtained from an average value of the amounts of moisture in the measurement sites P6 to P9. In addition, the reference moisture value can also be obtained from the median of the amounts of moisture in the measurement sites P1 to P5 and the target moisture value can also be obtained from the median of the amounts of moisture in the measurement sites P6 to P9.

For example, the reference moisture value and the target moisture value can be calculated based on the measurement values of the amounts of moisture which have been obtained by measuring the measurement sites in the moisture content measurement unit 1. In addition, the reference moisture value and the target moisture value can also be calculated based on the standardized values which have been obtained by standardizing the measurement values of the amounts of moisture as shown in FIGS. 2A and 2B.

The calculated reference moisture value and the target moisture value are output to the moisture decrease degree calculation unit 6 from the region moisture value calculation unit 5 and are stored in the storage unit 10.

The moisture decrease degree calculation unit 6 obtains the degree of decrease in moisture of the target moisture value with respect to the reference moisture value based on the reference moisture value and the target moisture value which have been calculated in the region moisture value calculation unit 5. This degree of decrease in moisture represents a degree of decrease in the level value of the amounts of moisture distributed in the lower region L with respect to the level value of the amounts of moisture distributed in the upper region U, and therefore, can be obtained based on, for example, the ratio of the target moisture value to the reference moisture value. In addition, the degree of decrease in moisture can also be obtained based on the difference between the reference moisture value and the target moisture value.

The obtained degree of decrease in moisture is output to the acne-affected skin determination unit 7 from the moisture decrease degree calculation unit 6 and is stored in the storage unit 10.

The acne-affected skin determination unit 7 determines the ease of generation of acne in the face of a subject by evaluating the degree of decrease in moisture obtained by the moisture decrease degree calculation unit 6 based on the index of the degree of decrease in moisture obtained by measuring the amounts of moisture in the face in advance.

For example, in a case where the degree of decrease in moisture is obtained based on the ratio of the target moisture value with respect to the reference moisture value, it is determined that acne is more easily generated as the degree of decrease in moisture is smaller. In addition, in a case where the degree of decrease in moisture is obtained based on the difference between the reference moisture value and the target moisture value, it is determined that acne is more easily generated as the degree of decrease in moisture is larger.

In addition, it is possible to evaluate the ease of generation of acne based on a threshold value of the degree of decrease in moisture which has been set in advance. The threshold value can be set to, for example, about 0.8 to 0.9 of the degree of decrease in moisture. Moreover, the threshold value may be fixed throughout the year or may be set and stored such that the threshold value changes depending on season.

The determination results of the acne-affected skin which have been obtained by the acne-affected skin determination unit 7 are output to the display control unit 8 which then displays the determination results on the display unit 9. In addition, the display control unit 8 can also display the amounts of moisture in the measurement sites P1 to P9 which have been stored in the storage unit 10, on the display unit 9 together with the determination results of the acne-affected skin.

According to the present embodiment, the acne-affected skin is determined by comparing the upper region U which has a constant amount of moisture in the face F of a subject with the lower region L in which the amount of moisture decreases in accordance with the progress of the acne-affected skin. Therefore, it is possible to accurately determine the acne-affected skin.

In the above-described embodiment, the upper region U of the face F of a subject was set to a reference region of the present invention, and the reference moisture value was obtained based on the amounts of moisture distributed in the upper region U and the target moisture value was obtained based on the amounts of moisture distributed in the lower region L. However, the present invention is not limited thereto. Specifically, the level of the amounts of moisture distributed in one of the upper region U or the lower region L can be set to a target moisture value based on the measurement values of the amounts of moisture in the upper region U and the lower region L and the level of the amounts of moisture distributed in a reference region using a region including the other of the upper region U and the lower region L as the reference region can be set to a reference moisture value. Moreover, it is possible to determine the ease of generation of acne in the face of a subject based on the degree of decrease in moisture or the degree of increase in moisture (degree of change in moisture) of the target moisture value with respect to the reference moisture value.

For example, the reference moisture value indicating the level of the amounts of moisture distributed in the entirety of the face and the target moisture value indicating the level of amounts of moisture distributed in the lower region L can be calculated based on values which have been obtained by measuring the amounts of moisture in the upper region U and the amounts of moisture in the lower region L after setting the entirety of the face of a subject to a reference region. Accordingly, it is possible to determine the acne-affected skin based on the degree of decrease in moisture of the target moisture value with respect to the reference moisture value.

In addition, the reference moisture value indicating the level of the amounts of moisture distributed in the lower region L and the target moisture value indicating the level of the amounts of moisture distributed in the upper region U can also be calculated after setting the lower region L of the face of a subject to a reference region. Accordingly, it is possible to determine the acne-affected skin based on the degree of increase in moisture of the target moisture value with respect to the reference moisture value.

In addition, the reference moisture value indicating the level of the amounts of moisture distributed in the entirety of the face and the target moisture value indicating the level of amounts of moisture distributed in the upper region U can also be calculated after setting the entirety of the face of a subject to a reference region. Accordingly, it is possible to determine the acne-affected skin based on the degree of increase in moisture of the target moisture value with respect to the reference moisture value.

The degree of increase in moisture can be obtained based on the ratio of the target moisture value to the reference moisture value or the difference between the reference moisture value and the target moisture value. In a case where the degree of increase in moisture is obtained based on the ratio of the target moisture value with respect to the reference moisture value, it is determined that acne is more easily generated as the degree of increase in moisture is larger. In addition, in a case where the degree of increase in moisture is obtained based on the difference between the reference moisture value and the target moisture value, it is determined that acne is more easily generated as the degree of increase in moisture is smaller.

Figure 4:
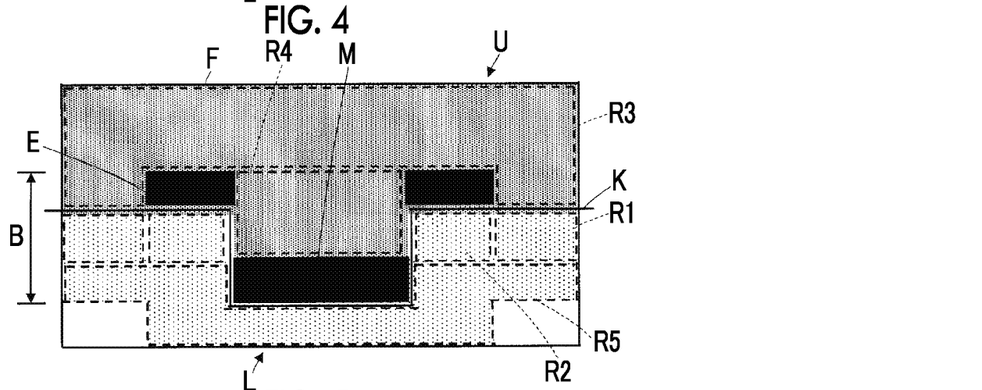
FIG. 4 is a view showing a modification example of the positions of an upper region and a lower region which are set with respect to the face of a subject.

In addition, the boundary line K which vertically divides the face F of a subject into two regions of the upper region U and the lower region L can be set so as to pass through the upper end portion of the cheek region R1, the upper end portion of the immediately below region R2 of the eye, and the lower end portion of the mouth as shown in FIG. 4. Accordingly, the upper region U is formed of the forehead region R3 and the nose region R4, and the lower region L is formed of the jaw skin region R5, the cheek region R1, and the immediately below region R2 of the eye. That is, the upper region U is formed of the divided regions A1 to A9 and the lower region L is formed of the divided regions A10 to A16.

Figure 5:
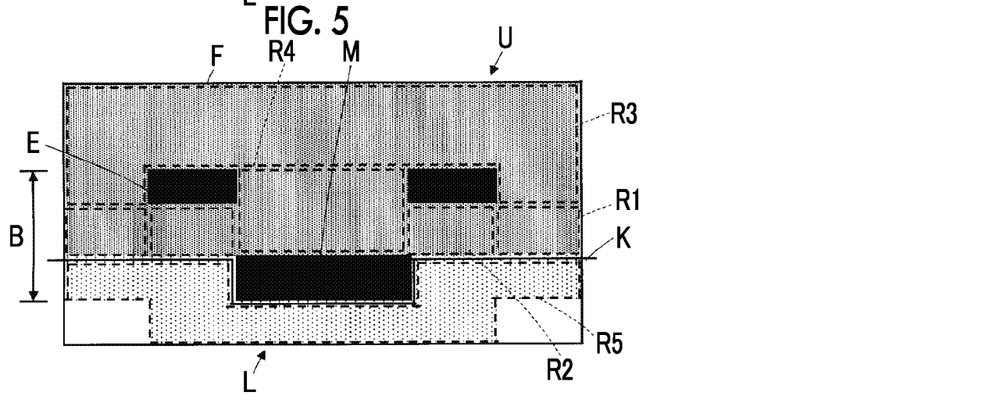
FIG. 5 is a view showing another modification example of the positions of an upper region and a lower region which are set with respect to the face of a subject.

In addition, the boundary line K can be set so as to pass through the upper end portion of the jaw skin region R5 as shown in FIG. 5. Accordingly, the upper region U is formed of the forehead region R3, the nose region R4, the immediately below region R2 of the eye, and the cheek region R1, and the lower region L is formed of the jaw skin region R5. That is, the upper region U is formed of the divided regions A1 to A11 and the lower region L is formed of the divided regions A12 to A16.

In addition, in the above-described embodiment, the moisture content measurement unit 1 is designed to measure the amount of moisture by making the tip portion of the probe 3 abut on the skin and detecting the electrostatic capacity in accordance with the amount of moisture in the skin. However, the present invention is not limited thereto as long as it is possible to measure the amount of moisture in the skin.

For example, it is also possible to measure the amount of moisture in the skin by detecting conductance in accordance with the amount of moisture in the horny layer of the skin using Skicon-100, Skicon-200 (registered trademark), and the like.

Furthermore, it is also possible to measure the amount of moisture in the skin through near-infrared measurement using absorption characteristics of a near-infrared region of moisture. The moisture has an absorption wavelength at 1400 nm. Therefore, it is possible to measure the face of a subject using, for example, a near infrared camera or a near-infrared spectral image measuring machine using a band-pass filter of 1400 nm, and to measure the amount of moisture from the measured face image.

In addition, in the above-described embodiment, the acne-affected skin determination device is constituted of the moisture content measurement unit 1 and the determination device main body 2, but can also have a configuration in which the moisture content measurement unit 1 is removed and data which has been obtained by measuring the amount of moisture in the face F of a subject is acquired to be input to the region moisture value calculation unit 5 of the determination device main body 2.

For example, the determination device main body 2 can be configured so as to be connected to a computer, in which the amount of moisture of the face F of a subject is stored, through a network; the acne-affected skin is determined based on the amount of moisture which has been input from the computer; and the determination results thereof are stored in a server or the like. Accordingly, a user can browse the determination results of the acne-affected skin by accessing the server or obtain the determination results of the acne-affected skin from the server through the network.

Here, an example of Examples in which the acne-affected skin is actually determined through the above-described acne-affected skin determination method will be shown.

In Examples, 12 subjects of 20 years of age or over were divided into a group (with the number of acne sites being 2 to 18) with acne and a group (with the number of acne sites being 0) without acne, and the amounts of moisture in the measurement sites P1 to P9 shown in FIG. 3 were measured. An average value (reference moisture value A1) of the amounts of moisture of the entirety of the face, an average value (reference moisture value A2) of the amounts of moisture in the upper region U, and an average value (target moisture value B) of the amounts of moisture in the lower region L were obtained based on the amounts of moisture in the measurement sites P1 to P9 which have been measured and obtained. Then, the degree of decrease in moisture (target moisture value B/reference moisture value A1 or target moisture value B/reference moisture value A2) was calculated based on the ratio of the target moisture value B with respect to the reference moisture value A1 or A2. The results in which the average values are obtained from the group with acne and the group without acne based on these values which have been calculated for each subject were shown in Table 1.

In Example 1, the boundary line K dividing the upper region U and the lower region L was set so as to pass through the upper end portion of the cheek region R1, the lower end portion of the immediately below region R2 of the eye, and the lower end portion of the mouth M as shown in FIG. 3. In Example 2, the boundary line K was set so as to pass through the upper end portion of the cheek region R1, the upper end portion of the immediately below region R2 of the eye, and the lower end portion of the mouth M as shown in FIG. 4. In Example 3, the boundary line K was set so as to pass through the upper end portion of the jaw skin region R5 as shown in FIG. 5.

TABLE 1

|  |  | There is acne | | There is no acne | | |
|---|---|---|---|---|---|---|
|  |  | Average value | Standard deviation | Average value | Standard deviation | Correlation coefficient |
|  | Number of acne sites | 9.5 | 6.8 | 0.0 | 0.0 |  |
|  | Reference moisture value A1 | 55.2 | 7.5 | 59.1 | 9.4 | −0.10 |
| Example 1 | Reference moisture value A2 | 57.1 | 8.2 | 58.8 | 11.7 | 0.12 |
|  | Target moisture value B | 51.9 | 8.6 | 59.5 | 5.2 | −0.50 |
|  | Target moisture value B/reference moisture value A1 | 0.91 | 0.14 | 1.03 | 0.14 | −0.67 |
|  | Target moisture value B/reference moisture value A2 | 0.94 | 0.09 | 1.02 | 0.08 | −0.67 |

TABLE 1-continued

|  |  | There is acne | | There is no acne | | |
|---|---|---|---|---|---|---|
|  |  | Average value | Standard deviation | Average value | Standard deviation | Correlation coefficient |
| Example 2 | Reference moisture value A2 | 56.5 | 8.3 | 57.8 | 12.7 | 0.21 |
|  | Target moisture value B | 54.0 | 8.6 | 60.4 | 6.3 | −0.43 |
|  | Target moisture value B/reference moisture value A1 | 0.96 | 0.15 | 1.07 | 0.16 | −0.67 |
|  | Target moisture value B/reference moisture value A2 | 0.98 | 0.08 | 1.03 | 0.07 | −0.68 |
| Example 3 | Reference moisture value A2 | 57.7 | 8.1 | 60.0 | 11.1 | 0.09 |
|  | Target moisture value B | 49.1 | 9.2 | 56.7 | 5.4 | −0.54 |
|  | Target moisture value B/reference moisture value A1 | 0.85 | 0.15 | 0.96 | 0.11 | −0.67 |
|  | Target moisture value B/reference moisture value A2 | 0.89 | 0.12 | 0.97 | 0.08 | −0.67 |

As shown in Table 1, in Examples 1 to 3, it was found that the reference moisture value A2 in the group with acne indicated the same value as that in the group without acne. In addition, the target moisture value B indicated the same value as that of the reference moisture value A2 in the group without acne, whereas the target moisture value B decreased in the group with acne. Accordingly, it was considered that, in the faces F of subjects with a large amount of acne, decrease in the amount of moisture in accordance with the acne-affected skin is caused in the lower region L while a constant amount of moisture is kept in the upper region U.

Figure 6:
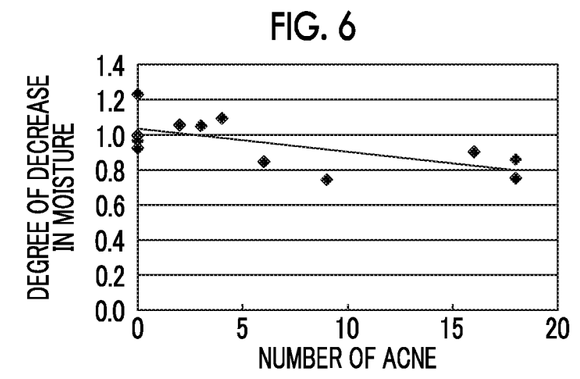
FIG. 6 is a view in which the change in the degree of decrease in moisture which has been calculated from the ratio of a target moisture value to a reference moisture value with respect to the number of acne sites is obtained.

In addition, it was found that the degree of decrease in moisture of the target moisture value B with respect to the reference moisture value A1 or A2 significantly decreased in the group with acne with respect to the group without acne. Here, in Example 1, the results in which the values of the degrees of decrease in moisture with respect to the number of acne sites are plotted are shown in FIG. 6. In this manner, it can be seen that the values of the degrees of decrease in moisture in accordance with the increase in the number of acne sites decrease, and therefore, there is a high correlation therebetween. In reality, in Examples 1 to 3, regarding the correlation coefficient shown in Table 1 in which the correlation with respect to the number of acne sites were obtained, the reference moisture values A1 and A2 indicated low values of −0.10 to 0.21, whereas the degrees of decrease in moisture indicated high values of −0.67 to −0.68. Therefore, it was found that there was a high correlation between the number of acne sites and the degree of decrease in moisture.

Accordingly, it can be seen that the acne-affected skin is determined using the ratio of the target moisture value B to the reference moisture value A1 or A2 as a degree of decrease in moisture, and therefore, it is possible to accurately determine the acne-affected skin.

Figure 7:
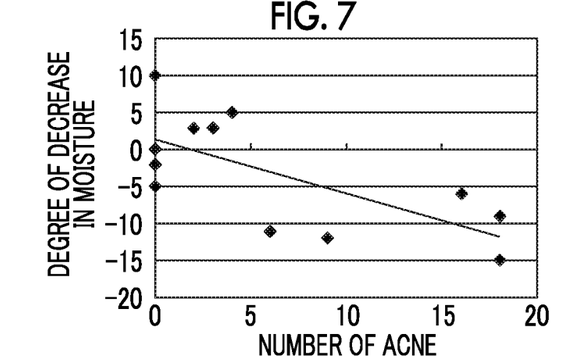
FIG. 7 is a view in which the change in the degree of decrease in moisture which has been calculated from the difference between the reference moisture value and the target moisture value with respect to the number of acne sites is obtained.

Even in a case where the degree of decrease in moisture was calculated based on the difference between the reference moisture value A1 or A2 and the target moisture value B, a high correlation was recognized between the number of acne sites and the degree of decrease in moisture. Regarding Example 1, the results in which the values of the degrees of decrease in moisture, which have been calculated based on the difference between the reference moisture value and the target moisture value, with respect to the number of acne sites are plotted are shown in FIG. 7. In this manner, the values of the degrees of decrease in moisture in accordance with the increase in the number of acne sites decreased, and the correlation coefficient therebetween was 0.5, showing a high correlation.

Accordingly, it can be seen that the acne-affected skin is determined using the difference between the reference moisture value A1 or A2 and the target moisture value B as a degree of decrease in moisture, and therefore, it is possible to accurately determine the acne-affected skin.

Figure 8:
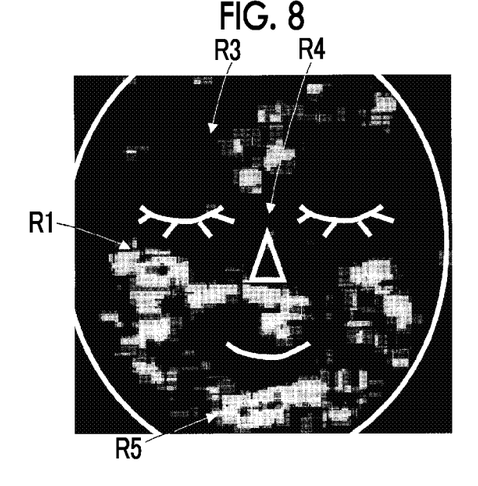
FIG. 8 is a view showing a distribution of acne in the face of a subject.

Furthermore, in FIG. 8, the positions of acne sites generated in 25 subjects of 20 years of age or over are represented by white spots, which are then shown by being displayed in an overlapping manner. In this manner, it can be seen that, in regard to the subjects of 20 years of age or over, the number of acne sites generated in the T-zone including the forehead region R3 and the nose region R4 is small whereas the number of acne sites generated in the U-zone including the cheek region R1 of the face, the immediately below region R2 of the eye, and the jaw skin region R5 is large. Particularly, a large amount of acne was observed in the cheek region R1 and around the mouth within the jaw skin region R5.

Accordingly, it was suggested that acne was easily generated in the U-zone of the face for the subjects of 20 years or over, and this is a factor that causes a decrease in the amounts of moisture distributed in the lower region L with respect to the amounts of moisture distributed in the upper region U of the face.

Embodiment 2

In Embodiment 1, the acne-affected skin was determined based on the decrease in the amounts of moisture in the lower region L with respect to the upper region U of the face of target subjects whose acne-affected skin had been continuing over a certain period of time. However, the acne-affected skin can also be determined based on the decrease in the amounts of moisture of the lower region L with respect to the upper region U of subjects with acne temporarily generated.

Figure 9A:
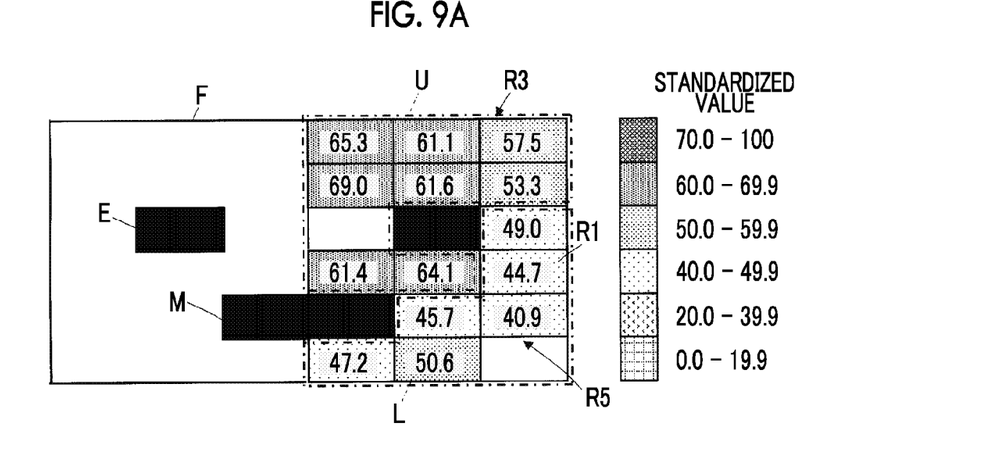
FIG. 9A is a view showing a distribution of the amount of moisture in the face of a subject with a large amount of acne in an acne-affected skin determination method according to Embodiment 2 immediately before menstruation and FIG. 9B is a view showing a distribution of the amount of moisture after menstruation.
Figure 9B:
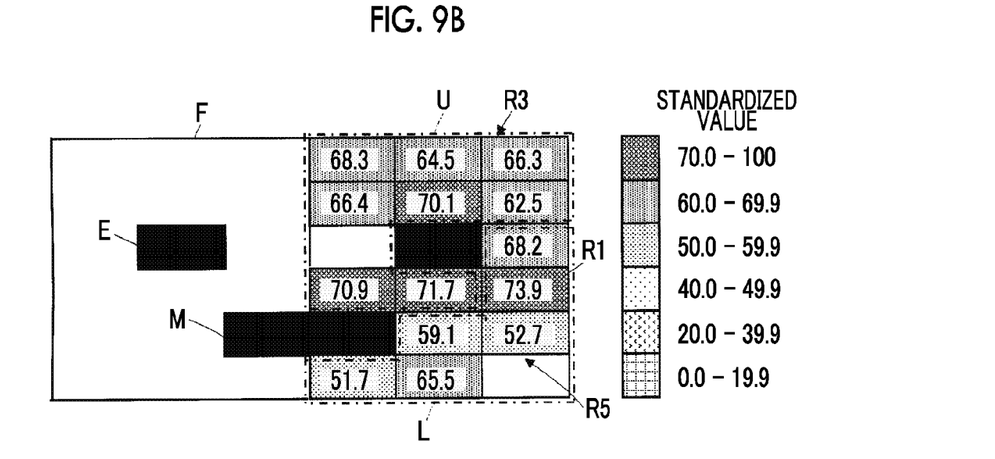
Figure 10A:
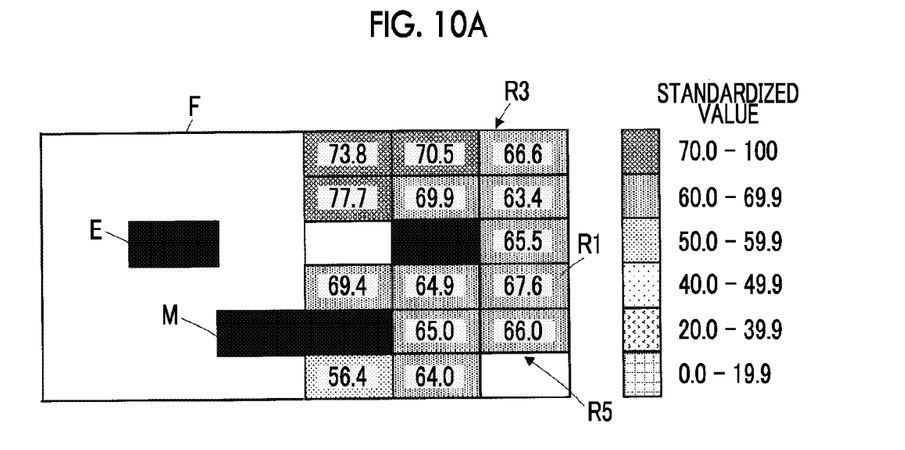
FIG. 10A is a view showing a distribution of the amount of moisture in the face of a subject with a small amount of acne in the acne-affected skin determination method according to Embodiment 2 immediately before menstruation and FIG. 10B is a view showing a distribution of the amount of moisture after menstruation.
Figure 10B:
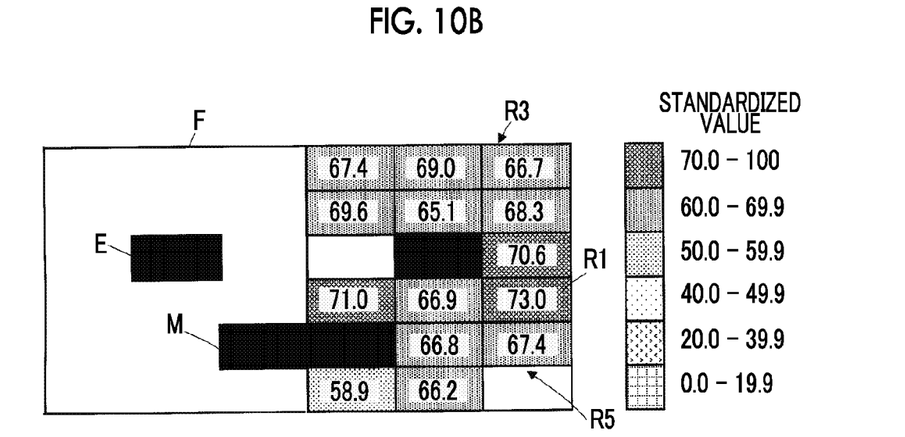

For example, it is known that the states of the skins of female subjects change in accordance with the menstrual cycle. The distributions of the amounts of moisture immediately before menstruation and after menstruation in subjects with a large amount of acne are shown in FIGS. 9A and 9B and the distributions of the amounts of moisture immediately before menstruation and after menstruation in subjects with a small amount of acne are shown in FIGS. 10A and 10B. FIGS. 9A to 10B are views in which the amounts of moisture in divided regions A1 to A6 and A8 to A15 out of divided regions A1 to A16 in which the left half section of the face F of target subjects of 20 years of age or over is divided into sixteen regions, are actually measured, the obtained amounts of moisture are standardized within a range of 0.0 to 100.0, and the divided regions A1 to A6 and A8 to A15 are distinguished and shown in accordance with the standardized values.

As shown in FIG. 9A, the amounts of moisture distributed in the face F of a subject with a large amount of acne immediately before menstruation indicate high standardized values of greater than or equal to 53 in the divided regions A1 to A6, A9, and A10 included in the upper region U. In contrast, the amounts of moisture thereof indicate low standardized values within a range of 40.0 to 51.0 in the divided regions A8, A11 to A15 included in the lower region L. On the other hand, as shown in FIG. 9B, the amounts of moisture distributed in the face F of the subject with a large amount of acne indicate high values in many divided regions A1 to A6 and A8 to A15 after menstruation, and therefore, no significant change has been found in the upper region U and the lower region L of the face.

In contrast, as shown in FIGS. 10A and 10B, the amounts of moisture distributed in the face F of the subject with a small amount of acne immediately before menstruation and after menstruation indicate high values in all of the divided regions A1 to A6 and A8 to A15, and therefore, no significant change has been found in the upper region U and the lower region L of the face.

Accordingly, it can be seen that the level of the amounts of moisture in the lower region L with respect to the upper region U does not almost change immediately before menstruation and after menstruation of the subject with a small amount of acne, whereas the amounts of moisture in the lower region L with respect to the upper region U temporarily decrease within a predetermined period of time immediately before menstruation of the subject with a large amount of acne.

Figure 11:
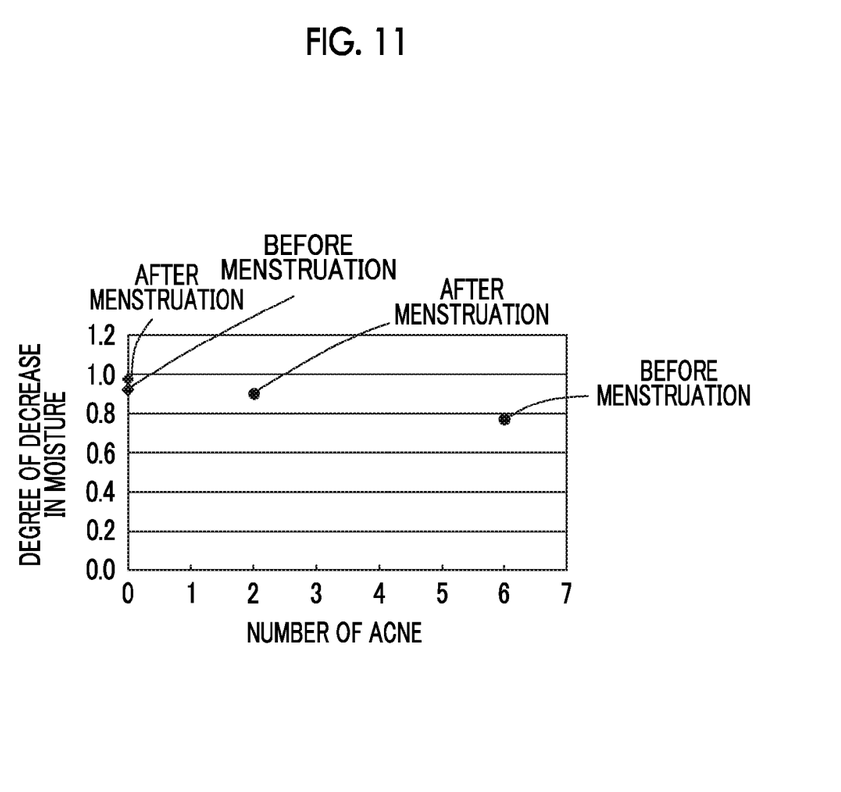
FIG. 11 is a view in which the change in the degree of decrease in moisture which has been calculated from the ratio of a target moisture value to a reference moisture value with respect to the number of acne sites before and after menstruation is obtained.

In reality, the amounts of moisture of the faces of a subject with a large amount of acne and a subject with a small amount of acne immediately before menstruation and after menstruation are measured, and the results in which the values of the degrees of decrease in moisture with respect to the number of acne sites are plotted are shown in FIG. 11. Here, the amounts of moisture of the face in the measurement sites P1 to P9 were measured as shown in FIG. 3. In addition, the setting of the upper region U and the lower region L with respect to the face of the subject was performed such that the boundary line K passes through the upper end portion of the cheek region R1, the lower end portion of the immediately below region R2 of the eye, and the lower end portion of the mouth M as shown in FIG. 3. In FIG. 11, the results which have been obtained by performing measurement on the subject with a large amount of acne were represented by ● and the results which have been obtained by performing measurement on the subject with a small amount of acne were represented by ◆.

As shown in FIG. 11, it can be seen that, in regard to the subject with a large amount of acne, 6 sites of acne generated immediately before menstruation decreased to two sites after menstruation and the degree of decrease in moisture increased in accordance with the decrease in the number of acne sites. In addition, even in regard to the subject with a small amount of acne, the degree of decrease in moisture after menstruation with respect to the degree of decrease in moisture immediately before menstruation slightly increased.

Accordingly, it is suggested that the amounts of moisture in the lower region L with respect to the upper region U in the faces of the subjects temporarily change before and after menstruation. In addition, it can be seen that the increase in the degree of decrease in moisture after menstruation of the subject with a small amount of acne with respect to the degree of decrease in moisture immediately before menstruation is small whereas the increase in the degree of decrease in moisture after menstruation of the subject with a large amount of acne with respect to the degree of decrease in moisture immediately before menstruation is large. Accordingly, the amount of moisture of the face of the subject with a large amount of acne before and after menstruation significantly changes, and it is considered that this change is caused by temporary significant decrease of the amounts of moisture in the lower region L with respect to the upper region U immediately before menstruation.

Therefore, it is possible to determine the ease of generation of acne before menstruation based on the amounts of moisture of the face of a subject within a predetermined period of time immediately before menstruation.

That is, the amounts of moisture in the face F of a subject within a predetermined period of time immediately before menstruation are measured by the moisture content measurement unit 1 of the acne-affected skin determination device shown in FIG. 1, and the values of the amounts of moisture are output to the region moisture value calculation unit 5 of the determination device main body 2 from the moisture content measurement unit 1. The region moisture value calculation unit 5 calculates the reference moisture value indicating the level of the amounts of moisture distributed in the upper region U of the face of the subject and the target moisture value indicating the level of the amounts of moisture distributed in the lower region L, based on the amounts of moisture which have been input from the moisture content measurement unit 1.

The reference moisture value and the target moisture value which have been calculated by the region moisture value calculation unit 5 are output to the moisture decrease degree calculation unit 6 which then obtains the degree of decrease in moisture of the target moisture value with respect to the reference moisture value. Then, the acne-affected skin determination unit 7 determines the ease of generation of acne in the face of a subject before menstruation, based on the degree of decrease in moisture.

According to the present embodiments, it is possible to accurately determine the ease of generation of acne immediately before menstruation with respect to a subject whose skin state of the face significantly changes in accordance with the menstrual cycle.

EXPLANATION OF REFERENCES

1: moisture content measurement unit,
2: determination device main body,
3: probe,
4: moisture content calculation unit,
5: region moisture value calculation unit,
6: moisture decrease degree calculation unit,
7: acne-affected skin determination unit,
8: display control unit,
9: display unit,
10: storage unit,
11: control unit,
12: operating unit,
F: face,
M: mouth,
E: eye,
A1 to A16: divided region,
N1, N2: vertical line,
N3 to N7: horizontal line, P1 to P9: measurement site,
U: upper region,
L: lower region,
B: boundary range,
R1: cheek region,
R2: immediately below region of eye,
R3: forehead region,
R4: nose region,
R5: jaw skin region.

What is claimed is:

1. An acne-affected skin determination method comprising:
    setting an upper region and a lower region so as to vertically divide the face of a subject into two regions,
    acquiring amount of moisture of a plurality of measurement sites in the lower region;
    acquiring amount of moisture of a plurality of measurement sites in the upper region;
    calculating an average value of the amounts of moisture of the plurality of measurement sites in one of the upper region or the lower region as a target moisture value, setting a region including the other of the upper region and the lower region as a reference region and calculating an average value of the amounts of moisture of the plurality of measurement sites;
    obtaining a difference in moisture of the target moisture value with respect to the reference moisture value; and
    determining the ease of generation of acne in the face of the subject based on the difference in moisture obtained.

2. The acne-affected skin determination method according to claim 1,
    wherein the target moisture value indicates the average value of the amounts of moisture of the plurality of measurement sites in the lower region and the reference moisture value indicates the average value of the amounts of moisture of the plurality of measurement sites in the upper region.

3. The acne-affected skin determination method according to claim 1,
    wherein the target moisture value indicates the average value of the amounts of moisture of the plurality of measurement sites in the lower region and the reference moisture value indicates the average value of the amounts of moisture of the plurality of measurement sites in a region of the entirety of the face.

4. The acne-affected skin determination method according to claim 1,
    wherein, with respect to a half section of the face of the subject in which the face is divided into a left region and a right region by a central vertical line, the half section of the face is divided horizontally into three regions using a first vertical line which passes through the corner of the mouth from an inner corner of an eye and a second vertical line which passes through an outer corner of the eye, and the half section of the face is divided vertically into six regions using a first horizontal line which vertically divides the forehead into two regions, a second horizontal line which passes through an upper end portion of the eye, a third horizontal line which passes through a lower end portion of the eye, a fourth horizontal line which passes through an upper end portion of the mouth, and a fifth horizontal line which passes through a lower end portion of the mouth, so as to divide the half section of the face into sixteen regions except for the eye and the mouth,
    wherein the regions positioned on an upper side of the third horizontal line are set to regions A1 to A8, the regions positioned between the third horizontal line and the fourth horizontal line are set to regions A9 to A11 from the central portion to the side portion of the face, and the regions positioned on a lower side of the fourth horizontal line are set to regions A12 to A16, and
    wherein the upper region and the lower region are set based on the regions A1 to A16.

5. The acne-affected skin determination method according to claim 4,
    wherein the upper region is formed of the regions A1 to A10 and the lower region is formed of the regions A1 to A16.

6. The acne-affected skin determination method according to claim 4,
    wherein the upper region is formed of regions A1 to A9 and the lower region is formed of regions A10 to A16.

7. The acne-affected skin determination method according to claim 4,
    wherein the upper region is formed of regions A1 to A11 and the lower region is formed of regions A12 to A16.

8. The acne-affected skin determination method according to claim 1,
    wherein the target moisture value and the reference moisture value are respectively obtained based on the amounts of moisture in the lower region and the amounts of moisture in the upper region which have been measured within a predetermined period of time immediately before menstruation.

9. A acne-affected skin determination device comprising:
    a region moisture value calculation unit which sets an upper region and a lower region so as to vertically divide the face of a subject into two regions, acquires amount of moisture of a plurality of measurement sites in the lower region, acquires amount of moisture of a plurality of measurement sites in the upper region, and calculates an average value of the amounts of moisture of the plurality of measurement sites in one of the upper region or the lower region as a target moisture value, sets a region including the other of the upper region and the lower region as a reference region and calculates an average value of the amounts of moisture of the plurality of measurement sites in the reference region;
    a moisture difference calculation unit which obtains a difference in moisture of the target moisture value with respect to the reference moisture value;
    an acne-affected skin determination unit which determines the ease of generation of acne in the face of a subject based on the difference in moisture which is obtained by the moisture difference calculation unit, and
    a processor which controls each unit in the device.

* * * * *